United States Patent [19]
Meyer

[11] 3,956,395
[45] May 11, 1976

[54] DISTYRYLBENZENE DISULFONE DERIVATIVES

[76] Inventor: Hans Rudolf Meyer, Binningen, Switzerland

[22] Filed: Jan. 14, 1974

[21] Appl. No.: 433,177

[30] Foreign Application Priority Data
Jan. 23, 1973  Switzerland............................ 921/73

[52] U.S. Cl. .................... 260/607 A; 260/465 K; 260/488 CD; 260/470; 260/79; 8/1 W; 8/25; 8/62; 8/69; 8/63; 8/108; 8/115.6; 106/169; 106/196; 106/193 R
[51] Int. Cl.² ........................................ C07C 147/08
[58] Field of Search ................................ 260/607 A

[56] References Cited
UNITED STATES PATENTS
3,326,979  6/1967  Russell............................ 260/607 A

FOREIGN PATENTS OR APPLICATIONS
| | | | |
|---|---|---|---|
| 992,800 | 10/1951 | France............................ | 260/607 A |
| 1,415,977 | 10/1963 | France............................ | 260/607 A |
| 1,583,595 | 11/1969 | France............................ | 260/607 A |
| 1,297,775 | 5/1962 | France............................ | 260/607 A |

*Primary Examiner*—Lewis Gotts
*Assistant Examiner*—D. R. Phillips
*Attorney, Agent, or Firm*—Joseph C. Kolodny

[57] ABSTRACT

The present invention provides new 1,4-distyrylbenzene derivatives corresponding to the formula

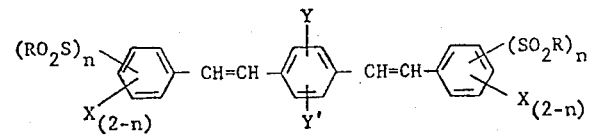

wherein R represents alkyl with 1 to 8 carbon atoms which is optionally substituted by non-chromophoric radicals, phenyl which is optionally substituted by non-chromophoric radicals, alkenyl with 2 to 4 carbon atoms or cycloalkyl with 5 or 6 carbon atoms, X represents hydrogen, chlorine, or alkyl with 1 to 4 carbon atoms, Y and Y' each independently represents hydrogen, chlorine, methyl, methoxy or ethoxy, and $n$ is 1 or 2. The new compounds are valuable optical brighteners for organic materials, especially for polyesters.

6 Claims, No Drawings

DISTYRYLBENZENE DISULFONE DERIVATIVES

The present invention relates to new 1,4-distyrylbenzene derivatives, their manufacture and their use as optical brighteners for organic materials.

These new 1,4-distyrylbenzene derivatives have the formula

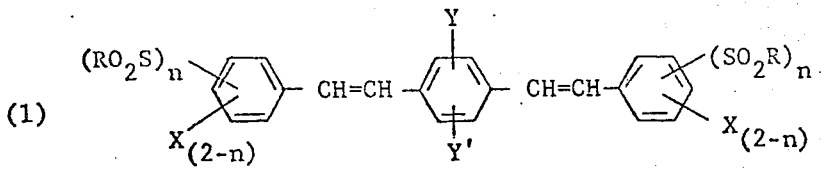

(1)

wherein R represents alkyl with 1 to 8, preferably 1 to 4, carbon atoms which is optionally substituted by non-chromophoric radicals, phenyl which is optionally substituted by non-chromophoric radicals, alkenyl with 2 to 4 carbon atoms or cycloalkyl with 5, or preferably 6, carbon atoms, X represents hydrogen, chlorine, or alkyl with 1 to 4 carbon atoms, Y and Y' each independently represents hydrogen, chlorine, methyl, methoxy or ethoxy, and $n$ is 1 or 2.

Non-chromophoric substituents are naturally not taken into account in the limitation of the number of carbon atoms to 1 to 8, preferably 1 to 4, in respect of alkyl. The number of carbon atoms of substituted alkyl increases accordingly by the number of carbon atoms of the respective substituent. As non-chromophoric radicals which are possible substituents for an alkyl radical R, there may be cited primarily hydroxy, cyano, chlorine, carboxy, carbalkoxy with 2 to 19, preferably 2 to 5, carbon atoms, acyloxy with 2 to 5 carbon atoms, or alkyl or alkoxy with 1 to 18, preferably 1 to 4, carbon atoms, or aryl, preferably phenyl which is optionally substituted by halogen, in particular chlorine, alkyl or alkoxy with 1 to 4 carbon atoms; further non-chromophoric substituents of importance are e.g. sulpho, aryloxy, aralkyloxy, alkenyloxy, carbaryloxy and carbaralkyloxy. A substituted alkyl radical can be poly-substituted by one or more substituents. As a rule, the alkyl radical is substituted not more than twice. Examples of such substituted alkyl radicals are 2-hydroxyethyl, 2,3-dihydroxypropyl, —CH$_2$COOCH$_2$C$_6$H$_5$, —CH$_2$COOC$_6$H$_5$, —CH$_2$CH$_2$COOC$_6$H$_5$, —CH$_2$CH$_2$COOCH$_2$C$_6$H$_5$, carbalkoxy (1-4C)methyl, carbalkoxy-(1-4C)ethyl, cyanomethyl, cyanoethyl, alkoxy(1-4C)ethyl phenoxyethyl, benzyloxyethyl, chloromethyl, dichloromethyl, 2-sulphoethyl, 3-sulphopropyl, 4-sulphobutyl, benzyl, chlorobenzyl, dichlorobenzyl, diphenylmethyl, triphenylmethyl.

Suitable non-chromophoric substituents of the phenyl radical are chiefly phenyl and, in particular, halogen, preferably chlorine, alkyl and alkoxy with 1 to 6, preferably 1 to 4, carbon atoms. The number of these non-chromophoric substituents per phenyl radical can be up to 3, but in general is not more than 2. Examples of alkenyl radicals are vinyl, allyl, methallyl, crotyl.

Within the scope of the formula (1), particular interest attaches to compounds of the formula

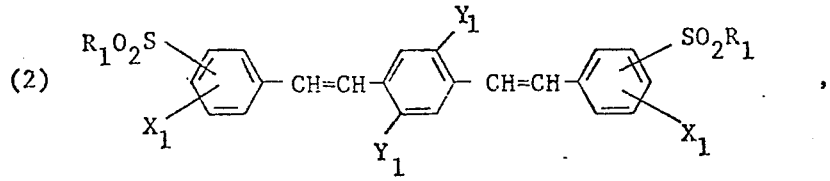

(2)

wherein R$_1$ represents alkyl with 1 to 6, preferably 1 to 4, carbon atoms which is optionally substituted chlorine, hydroxy, cyano, acyloxy with 2 to 5 carbon atoms or carbalkoxy with 2 to 5 carbon atoms, cyclohexyl, benzyl which is optionally substituted in the phenyl moiety by chlorine or methyl, or phenyl which is optionally substituted by chlorine, bromine, or alkyl with 1 to 6, preferably 1 to 4, carbon atoms, X$_1$ represents hydrogen, chlorine, methyl, or alkylsulphonyl with 1 to 4 carbon atoms, and Y$_1$ represents hydrogen, chlorine, methyl or methoxy, and to compounds of the formula

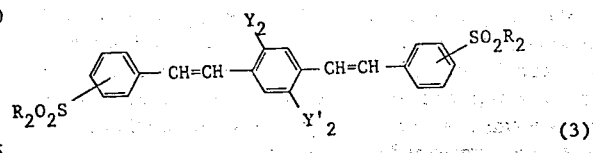

(3)

wherein R$_2$ represents alkyl with 1 to 6 carbon atoms which is optionally substituted by acyloxy with 2 to 5 carbon atoms, cyclohexyl, benzyl which is optionally substituted in the phenyl moiety by chlorine or methyl, or phenyl which is optionally substituted by chlorine or alkyl with 1 to 6 carbon atoms, and Y$_2$ and Y$_2$' each independently represents hydrogen or chlorine.

Particularly preferred compounds within the scope of formula (3) are those wherein Y$_2$ and Y$_2$' represent hydrogen and R$_2$ represents alkyl with 1 to 6 carbon atoms, cyclohexyl or benzyl.

In the formulae (1), (2), and (3), the symbol Y and Y', Y$_1$, Y$_2$ and Y$_2$' X and X$_1$ preferably represent hydrogen Classes of compounds of primary importance have the formulae

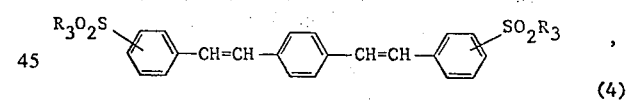

(4)

wherein R$_3$ represents alkyl with 1 to 6, preferably 1 to 5, carbon atoms, or phenyl which is optionally substituted by chlorine or alkyl with 1 to 6, preferably 1 to 4, carbon atoms,

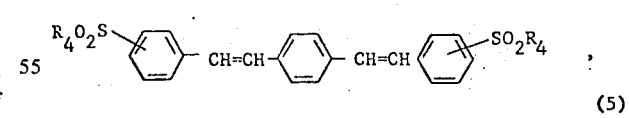

(5)

wherein R$_4$ represents alkyl with 1 to 6, preferably 1 to 5, carbon atoms which is optionally substituted by chlorine, cyano, hydroxy, acyloxy with 2 to 5 carbon atoms, or carbalkoxy with 2 to 5 carbon atoms, or represents cyclohexyl, and (6) 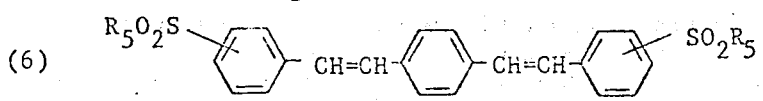

wherein $R_5$ represents alkyl with 1 to 6, preferably 1 to 4, carbon atoms.

The radicals $-SO_2R$, $-SO_2R_1$, $-SO_2R_2$, $-SO_2R_3$, $-SO_2R_4$ and $-SO_2R_5$ in the formulae (1) to (6) are preferably in the meta-position, and especially in the para-position, to the vinyl bridge.

Compounds having a particularly interesting utility are those of the formula (7) 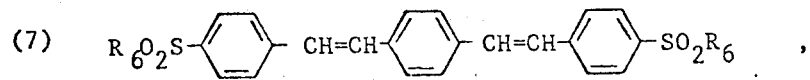

wherein $R_6$ represents alkyl with 1 to 6, preferably 1 to 4, carbon atoms, or phenyl. The preferred significance is alkyl.

The distyrylbenzenes of the formula (1) and of the secondary formulae (2) to (7) characterised hereinbefore can be manufactured by various processes which are known per se. For example, it is possible to manufacture the compounds by reacting one molar equivalent of a compound of the formula (8) 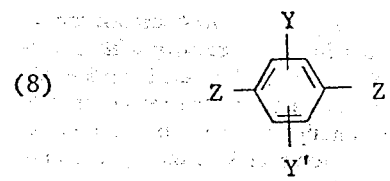

with 2 molar equivalents of a compound of the formula (9) 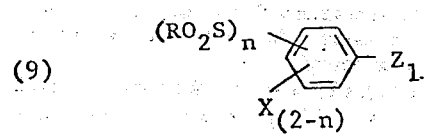

in which formulae the symbols R, X, Y, Y' and $n$ have the meanings given hereinbefore and one of symbols Z and $Z_1$ represents the group —CHO and the other represents one of the groups of the formulae

(10) 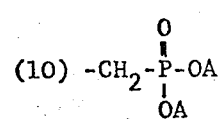  (11) 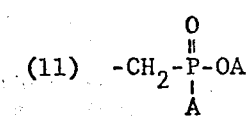

(12) 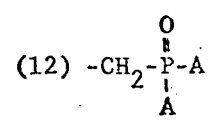  and  (13) 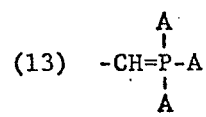

wherein A represents an optionally substituted alkyl, aryl, cycloalkyl or aralkyl radical.

Accordingly, it is therefore possible to react a terephthaladehyde of the formula

(14) 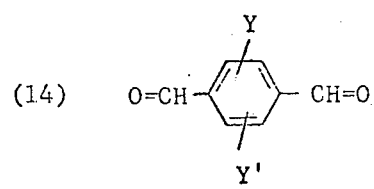

with a compound of the formula

(15) 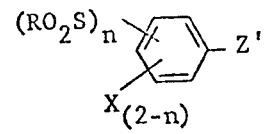

or a monoaldehyde of the formula

(16) 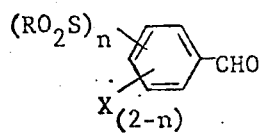

with a compound of the formula

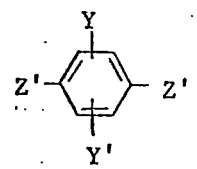

in which formulae Y, Y', R, X and n have the indicated meanings and Z' represents one of the phosphorus containing radicals of the formulae (10), (11), (12) or (13).

The phosphorus compounds of the formulae (10) to (13) which are used herein as starting materials are obtained in known manner by reacting halomethyl compounds, preferably chloromethyl or bromomethyl compounds of the formula

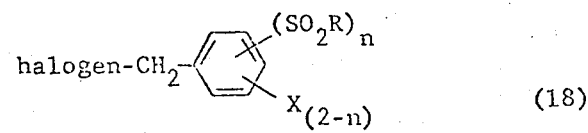 (18)

or

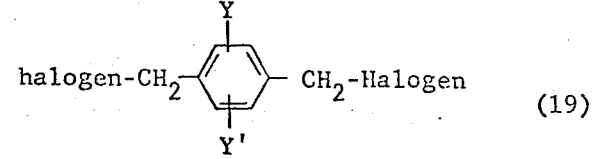 (19)

with phosphorus compounds of the formula

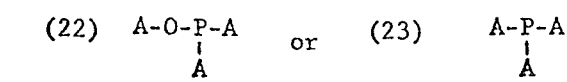

In these formulae, A has the indicated meaning, in which connexion radicals A bonded to oxygen preferably represent lower alkyl groups, radicals A directly bonded to phosphorus on the other hand are preferably aryl radicals, e.g. the benzene radical. The phosphorus compounds of the formula (12) can also be obtained by reaction of halomethyl compounds, preferably chloromethyl or bromomethyl compounds of the formulae (18) or (19), with P-chlorodiphenylphosphone and subsequent reaction with an alcohol of the formulae A–OH (wherein A has the meaning as defined hereinbefore), e.g. with methanol or with water.

The aldehydes used as starting materials are for the most part known. It is possible to manufacture the not yet described aldehydes in analogous manner to the known ones.

A modification of particular practical importance consists in using as phenylene components according to claim (8) those which have the formula

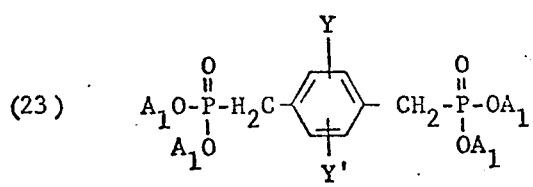

wherein $A_1$ represents an alkyl group with 1 to 4 carbon atoms.

The manufacturing process is advantageously carried out in inert solvents. examples of inert solvents are: hydrocarbons such as toluene and xylene, or alcohols, e.g. methanol, ethanol, isopropanol, butanol, glycols, glycol ethers. e.g. 2-methoxyethanol, hexanols, cyclohexanol and cyclooctanol, also ethers such as diisopropyl ether, tetrahydrofuran and dioxan, as well as dimethyl sulphoxide, formamide, and N-methylpyrrolidone. Particularly suitable are polar organic solvents, e.g. dimethyl formamide and dimethyl sulphoxide. It is also possible to carry out a number of the reactions in aqueous solution.

The temperature at which the reaction is carried out can vary within wide limits. It is determined by α. the resistance of the solvent employed to the reactants, especially to the strong basic alkali compounds,
β. the reactivity of the condensation partners, and
γ. the strength of the combination of solvent and base as condensation agent.

In practice, temperatures between 10°C and 100 °C are possible as a rule, especially if either dimethyl formamide or dimethyl sulphoxide is used as solvent. The preferred temperature range is between 20°C and 60°C. However, it is also possible to apply higher temperatures if this is desired in order to save time or if a less active but cheaper condensation agent is to be used. In principle, therefore, reaction temperature between 10°C and 180°C are also possible.

Suitable strong basic alkali compounds are chiefly the hydroxides, amides and alcoholates (preferably those of primary alcohols containing 1 to 4 carbon atoms) of alkali metals; for reasons of economy, those of lithium, sodium and potassium are of primary interest. However, in principle and in special cases it is also possible to use with success alkali sulphides and carbonates, arylalkali compounds, e.g. phenyl-lithium or strong amines (including ammonium bases, e.g. trialkylammonium hydroxides).

In many cases it is expedient to use the corresponding sulphide in place of a sulphone compound of the formula (9) or (15) to (18), and otherwise carrying out the procedure as described hereinbefore, in order to obtain the compounds of the formula (1) as intermediate step via compounds of the formula

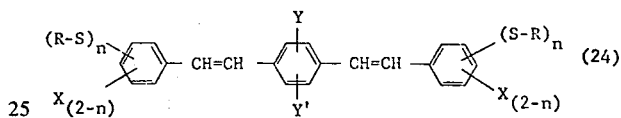

and subsequent oxidation thereof.

Both steps can also be carried out in the single step process without first isolating the disulphides, whereby in this case there is used for the first step a solvent which is inert to oxidation, e.g. chlorobenzene, toluene, dioxan etc. Examples of oxidants are hydrogen peroxide, peracids, such as peracetic acid, performic acid, perbenzoic acid; chromic acid, optionally in the presence of catalytic amounts of metal salts of vanadium, tungsten, molybdenum etc. Suitable solvents are organic acids, such as acetic acid, formic acid etc., optionally chlorinated aliphatic or aromatic hydrocarbons, dioxan, etc. and mixtures thereof. The temperature at which the oxidation is carried out can vary between room temperature and 200°C, depending on the reactivity of the oxidant, preferably between 50°C and 150°C. It is limited downwards by the decreasing solubility of the disulphiedes and upwards by the boiling point or decomposability of the reactants.

It is also possible to use the anil synthesis for the synthesis of compounds of the formula (1), wherein R represents phenyl which is optionally substituted by non-chromophoric substituents. For example, it is possible to manufacture compounds of the formula

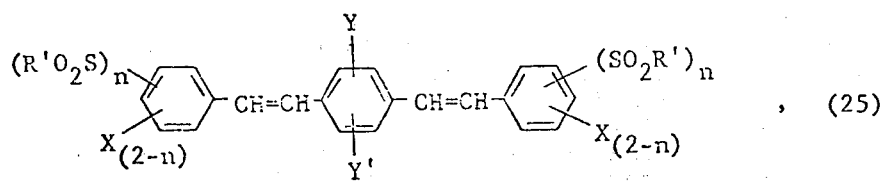

wherein R' represents a phenyl radical which is optionally substituted by non-chromophoric substituents and X, Y, Y' and n have the indicated meanings, by reacting a Schiff base of the formula

(26) 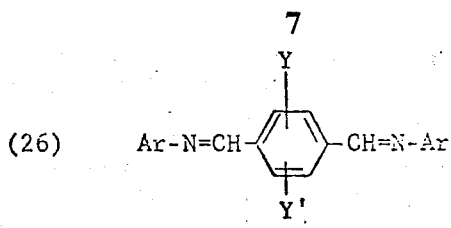

in which Ar represents an optionally substituted benzene radical, with 2 mols of a compound of the formula

(27) 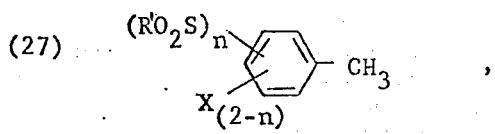

wherein R', X and n have the meanings given hereinbefore. The reaction is carried out in the presence of a strong basic alkali compound, dimethyl formamide being used as reaction medium, and, if alkali hydroxides are used as strong basic alkali compounds, these may have a water content of up to 25 percent.

A strong basic alkali compound is necessary for this reaction, by which are meant those compounds of the alkali metals (main group I of the Periodic System of the Elements), including ammonium, which have a strength approximating to at least that of lithium hydroxide. These can accordingly be compounds of lithium, sodium, rubidium, cesium or ammonium of the type, for example, of the alcoholates, hydroxides, amides, hydrides, sulphides or strong basic ion exchangers. It is advantageous to use (above all when mild reaction conditions with respect to the reaction temperature appear expedient) potassium compounds of the composition $$KOC_{x\text{-}1}H_{2x\text{-}1}$$

wherein $x$ is a whole number from 1 to 6, e.g. potassium hydroxide or potassium tert. butylate. In the case of alkali alcoholates, alkali amides (and hydrides), the process is to be carried out in practically anhydrous medium; but when using alkali hydroxides, water contents of up to 25 percent (e.g. water of crystallisation) are permissible. In the case of potassium hydroxide, a water content of up to about 15 percent has proved advantageous. Examples of other alkali compounds that can be used are sodium methylate, sodium hydroxide, sodium amide, lithium amide, lithium hydroxide, rubidium hydroxide, or cesium hydroxide. Naturally, it is also possible to carry out the process with mixtures of such bases.

The compounds of the formula (2) are advantageously reacted with the Schiff bases in the stoichiometric ratio 2:1, so that there is no substantial surplus of any component. It is advantageous to use at least the equivalent amount of the alkali compound, i.e. at least 2 mols of a compound with e.g. a KO group to 1 mol of Schiff base of the formula (26). Preferably the 4-to 8-fold amount is used when using potassium hydroxide.

The reaction according to the invention can ordinarily be carried out at temperatures between about 10°C and 150°C. If alcoholates are used during the reaction as potassium compound, then the reaction frequently takes place at room temperature, in which case it is not necessary to apply any external heat. When using potassium hydroxide, it is generally necessary to carry out the process at elevated temperature. For example, the reaction mixture is slowly heated to 30°–100°C and then kept at this temperature for a time, e.g. ½ hour to 2 hours. The final products can be processed from the reaction mixture by conventional, known methods.

Schiff bases which are preferably used have the formula

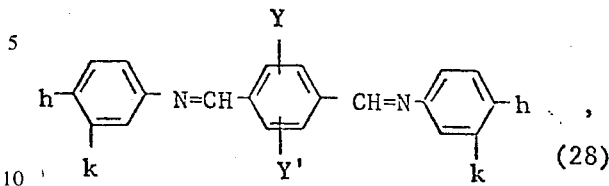 (28)

wherein $h$ and $k$ are the same or different and can represent hydrogen, chlorine, methoxy or alkyl with 2 to 4 carbon atoms.

The new compounds defined above show a more or less pronounced fluorescence in the dissolved or finely divided state. They can be used for the optical brightening of the most diverse synthetic, semi-synthetic or natural organic materials or substances which contain such organic materials.

As examples thereof there may be mentioned the following groups of organic materials, in so far as an optical brightening of these is possible, it being understood that the survey which follows is not intended to express any limitation:

I. Synthetic organic materials or high molecular weight:

a. polymerisation products based on organic compounds containing at least one polymerisable carbon-carbon double bond, that is to say their homopolymers or copolymers as well as their after-treatment products such as, for example, cross-linking, grafting or degradation products, polymer blends, or products obtained by modification of reactive groups, for example polymers based on α,β-unsaturated carboxylic acids or derivatives of such carboxykic acids, especially on acrylic compounds (such as, for example, acrylic esters, acrylic acid, acrylonitrile, acrylamides and their derivatives or their methacryl analogues), on olefine hydrocarbons (for example ethylene, propylene, styrenes or dienes and also so-called ABS polymers), and polymers based on vinyl and vinylidene compounds (for example vinyl chloride, vinyl alcohol and vinylidene chloride);

b. polymerisation products which can be obtained by ring opening, for example, polyamides of the polycaprolactam type, and also polymers which are obtained both through polyaddition and through polycondensation, such as polyethers or polyacetals, c. polycondensation products or precondensates based on bifunctional or polyfunctional compounds with condensable groups, their homocondensation and co-condensation products, and after-treatment products, for example polyester, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, for example alkyd resins) polyesters, polyamides (for example hexamethylenediamine adipate), maleate resins, melamine resins, their precondensates and analogous, polycarbonates and silicones;

d. polyaddition products such as polyurethanes (cross-linked and non-crosslinked) and epoxide resins.

II. Semi-synthetic organic materials, for example, cellulose esters of varying degrees of esterification (so-called 2 ½ acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and caseins.

The organic materials to be optically brightened can be in the most diverse states of processing (raw materials, semi-finished goods or finished goods). On the other hand, they can be in the form of structures of the most diverse shapes, for example predominantly three-dimensional bodies such as sheets, profiles, injection mouldings, various machined articles, chips, granules or foams, and also as predominantly two-dimensional bodies such as films, foils, lacquers, coattings, impregnations and coatins, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments yarns, threads, non-wovens, felts, waddings, flocked structures or woven textile fabrics, textile laminates, knitted fabrics and papers, cardboards or paper pulps.

The compounds to be used according to the invention are of importance, inter alia, for treatment of organic textile materials, especially woven textile fabrics. Where fibres, which can be in the form of staple fibres or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further auxiliaries can be added during the treatment.

Depending on the type of brightener compound used, it can prove advantageous to carry out the treatment in a neutral or alkaline or acid bath. The treatment is usually carried out at temperature of 20° to 140°C, for example at the boiling point of the bath or near it (about 90°C). Solutions or emulsions in organic solvents can also be used for the finishing according to the invention of textile substrates, as in practised in the dyeing industry in so-called solvent dyeing (pad-heat fixing application, or exhaustion dyeing processes in dyeing machines).

The new optical brighteners according to the present invention can further be added to, or incorporated in, the materials before or during their shaping. Thus they can for example be added to the compression moulding composition or injection moulding composition during the manufacture of films, sheets (for example working into polyvinyl chloride in a single roller mill) or mouldings.

Where fully synthetic or semi-synthetic organic materials are shaped by spinning processes or via spinning solutions/melts, the optical brighteners can be applied in accordance with the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The optical brighteners according to the present invention can, for example, also be employed in the following use forms:

a. mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints;

b. mixed with "carriers," wetting agents, plasticisers, swelling agents, anti-oxidants, ultraviolet absorbers, heat stabilisers and chemical bleaching agents (chlorite bleach or bleaching bath additives);

c. mixed with crosslinking agents or finishing agents (for example starch or synthetic finishes), and in combination with the most diverse textile finishing processes, especially synthetic resin finishes (for example creaseproof finishes such as wash-and-wear, permanent-press or non-iron), as well as flameproof finishes, soft handle finishes, antisoiling finishes or anti-static finishes, or antimicrobial finishes;

d. incorporation of the optical brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

e. as additives to master batches;

f. as additives to the most diverse industrial products in order to render these more marketable (for example improving the appearance of soaps, detergents, pigments);

g. in combination with other optically brightening substances;

h. in spinning bath preparations, that is to say as additives to spinning baths such as are used for improving the slip for the further processing of synthetic fibres, or from a special bath before the stretching of the fibre;

i. as scintillators for various purpose of a photographic nature, for example, for electrophotographic reproduction, for the optical brightening of photographic layers, optionally in combination with white pigments, for example $TiO_2$.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75°C, for example at room temperature, and to subject them to dry heat treatment at temperatures above 100°C, it being generally advisable additionally to dry the fibre material beforehand at a moderately elevated temperature, for example at not less than 60°C and up to about 130°C. The heat treatment in the dry state is then advantageously carried out at temperature between 120° and 225°C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, based on the material to be optically brightened, can vary within wide limits. It is possible to attain a distinct and durable effect even with very small amounts, in certain cases, for example, amounts of 0.0001 per cent by weight. However, amounts of up about 0.8 per cent by weight and optionally of up to about 2 per cent by weight can be employed. For most practical purposes, it is preferable to use amounts between 0.0005 and 0.5 per cent by weight.

In the following Examples which illustrate the invention, the parts and percentages are by weight, unless otherwise stated, and melting and boiling points are uncorrected, also in the absence of any contrary indication.

EXAMPLE 1

After expulsion of the air with nitrogen, 5.4 g of sodium methylate are added with stirring over the course of 15 minutes to a solution of 15.2 g of 4,4'-bis-(diethoxyphosphonomethyl)-benzene and 15.4 g of p-methylsulphonyl-benzaldehyde in 120 ml of dimethyl formamide. The mixture is stirred for 3 hours at 45°C, cooled, and treated with 30 ml of water. The precipitated product is filtered off with suction and washed repeatedly with methanol and water. It is then dried in vacuo to yield 5.0 g of the compound of the formula

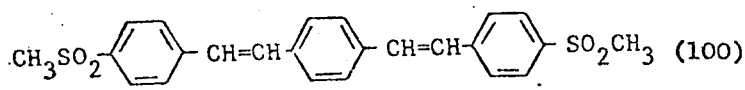

which melts at 394°C after recrystallisation from chlorinated bipheyl (Aroclor 1221, Monsanto) and dimethyl formamide. It is also possible to carry out the reaction in dimethyl sulphoxide instead of in dimethyl formamide. The sulphones of the formulae

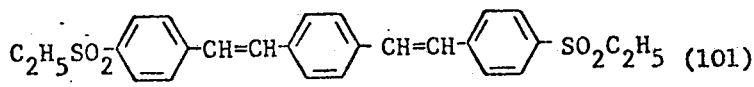

m.p. 297°C (after recrystallization from o-dichlorobenzene) and

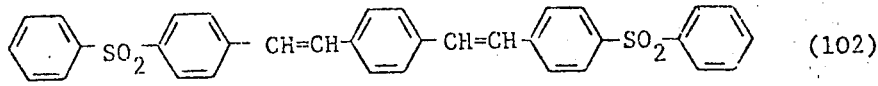

m.p. 343°C (after two recrystallisations from dimethyl formamide) are obtained by using p-ethylsulphonyl-benzaldehyde or p-phenylsulphonylbenzaldehyde instead of p-methylsulphonylbenzaldehyde and otherwise carrying out the process as described hereinabove.

The compound of the general formula (103) listed in Table 1 are obtained in analogous manner.

Table 1

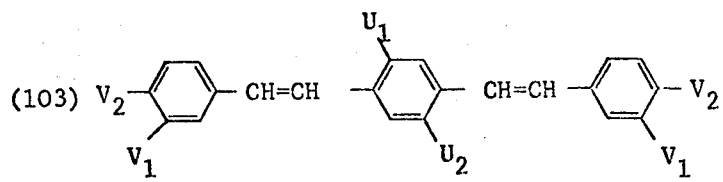

| formula | $V_1$ | $V_2$ | $U_1$ | $U_2$ | m.p. in °C |
|---|---|---|---|---|---|
| (104) | H | $-SO_2$-n-propyl | H | H | 282° |
| (105) | H | $-SO_2$-isobutyl | H | H | 287° |
| (106) | H | $-SO_2CH_3$ | $CH_3$ | $CH_3$ | 315° |
| (107) | H | $-SO_2CH_3$ | H | Cl | 283° |
| (108) | H | $-SO_2CH_3$ | Cl | Cl | 355° |
| (109) | H | —⟨⟩—Cl | H | H | 371° |
| (110) | $-SO_2CH_3$ | H | H | H | 263° |

EXAMPLE 2

6.86 g of 4-methyl-4'-isopropyl-diphenylsulphone and 3.55 g of the Schiff base consisting of 2 mols of aniline and 1 mol of terephthal aldehyde (melting point of the Schiff base: 160.5°–161.5°C) are stirred into 250 ml of dimethyl formamide in the absence of air and the reaction mixture is heated to 70°C. 5.6 g of potassium tert. butylate are added all at once to the resulting solution, which immediately turns a dark violet colour. The reaction mixture is stirred for 30 minutes at 70°C to 75°C and then cooled to about 20°C. After addition of 500 ml of methanol, the precipitated product is collected by suction filtration, washed with cold and then hot methanol and dried, to yield 3.9 g (48.8% of theory) of the compound of the formula

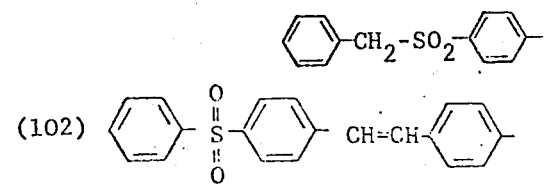

as a yellow powder which melts above 350°C. Two recrystallisations from o-dichlorobenzene (fuller's earth) yield 1.8 g (22.5% of theory) of fine, pale greenish yellow flakes with a melting point above 350°C.

It is also possible to manufacture the compound of the formula

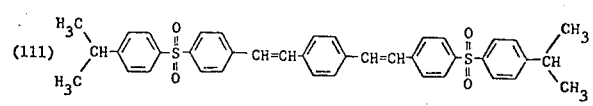

in similar mannner from phenyl-p-tolyl-sulphone. Two recrystallisations from o-dichlorobenzene (fuller's earth yield 1.15 g (16.4% of theory) of very fine greenish yellow needles which melt at 241°–342°C.

EXAMPLE 3

After expulsion of the air with nitrogen, 3.2 g of sodium methylate are added with stirring to a solution of 2.7 g of terephthal aldehyde and 15.3 g of crude ($\alpha$-diethoxyphosphono-p-tolyl)-methyl-sulphone in 50 ml of dimethyl formamide. The reaction mixture is stirred for 3 hours at 45°C, cooled, and treated with 25 ml of water. The precipitated product is collected by suction filtration, washed repeatedly with methanol and water, and dried in vacuo to yield 6.9 g of the compound of the formula (100), which, after two recrystallisations from dimethyl formamide, has a melting point of <400°C. The crude phosphonate of the formula

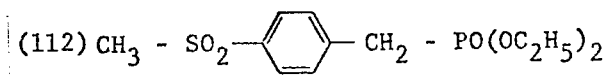

used as starting material is obtained in the following manner: 107 g of ($\alpha$-bromo-p-tolyl)-methyl-sulphone and 90 ml of triethylphosphite are gradually heated with stirring to reflux temperature. After the bulk of the ethyl chloride has been distilled off, the temperature is raised for 1/2 hour to 180°C and excess triethylphosphite is distilled off first at normal pressure and then under reduced pressure. As residue there are obtained 149.3 g of a pale yellow liquid, which is reacted with terephthal aldehyde without further purification.

EXAMPLE 4

Over the course of 1 hour, 12.9 ml of hydrogen peroxide (0.39 g/ml) in 20 ml of glacial acetic acid are added dropwise with vigorous stirring to a fine suspension of 16.1 g of the compound of the formula

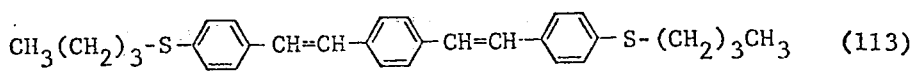

in 175 ml of chlorobenzene and 175 ml of glacial acetic acid, in the process of which the starting product rapidly passes into solution. After a further hour, 130 ml of solvent are distilled off, in the course of which a small amount of reaction product precipitates. After cooling to room temperature, collecting the product by suction filtration and washing the residue with 30 ml of chlorobenzene, there are obtained 14.2 g (77.5% of theory) of the compound of the formula

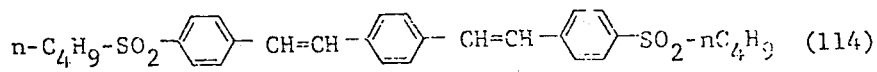

in the form of pale yellow crystals which melt at 287°C (after recrystallisation from chlorobenzene). The compound of the formula

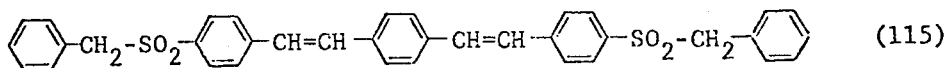

is obtained in analogous manner from the corresponding disulphide.

The disulphide of the formula (113) used as starting material is obtained as follows:

After expulsion of the air with nitrogen, 5.4 g of sodium methylate are added with stirring over the course of 15 minutes to a solution of 15.2 g of 1,4-bis-(diethoxyphosphonomethyl)-benzene and 16.3 g if p-(n-butylmercapto)-benzaldehyde in 200 ml of diemthyl formamide. The reaction mixture is stirred for 3 hours at 45°C, cooled, and treated with 10 ml of water. The precipitated product is collected by suction filtration and repeatedly washed with methanol and water. It is dried in vacuo to yield 14.7 g (89% of theory) of the compound of the formula (113), which, after two recrystallisations from chlorobenzene, melts at 271°C.

The p-(n-butylmercapto)-benzaldehyde used as starting material is obtained as follows:

With vigorous stirring, 269 ml of n-butyl-mercaptan are added dropwise to a mixture of 240 g of 49% potassium hydroxide solution and 300 ml of dimethyl sulphoxide, ensuring by water cooling that temperature does not rise above 50°C. While cooling is continued, 281 of p-chlorobenzaldehyde are added at 50°C and the reaction mixture is stirred overnight at 50°C and then briefly at 80°C. The batch is cooled to room temperature, then treated with 800 ml of water and 800 ml of carbon tetrachloride. The aqueous layer is isolated in a separating funnel and extracted with 200 ml of carbon tetrachloride. The combined carbon tetrachloride solutions are extracted twice with 500 ml of water on each occasion and dried with 30 g of sodium sulphate.

The solvent is evaporated off in a rotary evaporator and the residue is then fractionated in a high vacuum. After a first runnings of 50.8 g, there is obtained as distillate 331.6 g (83.3% of theory) of an almost colourless liquid of b.p. $_{1.1}$ = 124°–126°C.

The disulphones of the general formula (116) listed in Table II are obtained in analogous manner.

They are obtained from the corresponding disulphides of the general formula (126) listed in Table III. (Products which are readily soluble in dimethyl formamide require somewhat more water for their precipitation from this solvent).

Table II (116) 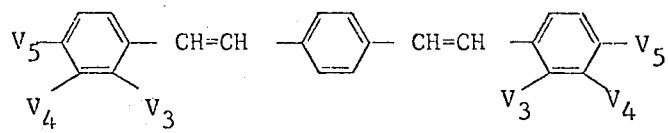

| formula | $V_3$ | $V_4$ | $V_5$ | m.p. in °C |
|---|---|---|---|---|
| (117) | $-SO_2CH_3$ | H | H | 225° |
| (118) | $-SO_2-CH(CH_2)_3$ | H | H | 234° |
| (119) | $-SO_2-C_2H_5$ | H | H | 177° |
| (120) | $-SO_2-\langle\rangle$ | H | H | 258° |
| (121) | H | Cl | $-SO_2CH_3$ | 304° |
| (122) | $-SO_2CH_3$ | H | $-SO_2CH_3$ | 331° |
| (123) | H | H | $-SO_2-n-C_6H_{13}$ | 266° |
| (124) | H | H | $-SO_2-\underset{CH_3}{CH}-C_2H_5$ | 314° |
| (125) | H | H | $-SO_2-\langle H\rangle$ | 350° |

Table III (126) 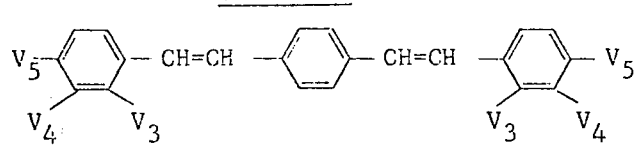

| formula | $V_3$ | $V_4$ | $V_5$ | m.p. in °C |
|---|---|---|---|---|
| (124) | $-SCH_3$ | H | H | 159° |
| (128) | $-S-CH(CH_3)_2$ | H | H | 101° |
| (129) | $-S-C_2H_5$ | H | H | 120° |
| (130) | $-S-\langle\rangle$ | H | H | 144° |
| (131) | H | Cl | $-SCH_3$ | 242° |
| (132) | H | H | $-S-CH_2CH_2OH$ | app. 319° |
| (133) | $-S-CH_2CH_2OH$ | H | H | 107° |
| (134) | $-SCH_3$ | H | $-SCH_3$ | 164° |
| (135) | H | H | $-S-nC_6H_{13}$ | 255° |
| (136) | H | H | $-S-\underset{CH_3}{CH}-C_2H_5$ | 211° |
| (137) | H | H | $-S-\langle H\rangle$ | 246° |

The alkyl- and phenyl-mercaptobenzaldehydes of the general formula (138) used for the manufacture of such disulphides are described in Table IV.

Table IV (138) 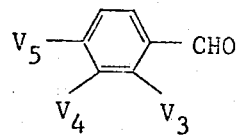

| $V_3$ | $V_4$ | $V_5$ | m.p. | recryst. from | b.p. |
|---|---|---|---|---|---|
| H | H | $CH_3S-$ | liquid | - | 137°/9 mm |
| H | H | $(CH_3)_2CH-CH_2-S-$ | " | - | 115°/0,4mm |
| $CH_3S-$ | H | H | " | - | 134°/10mm |
| $CH_3S-$ | H | $CH_3S-$ | 70° | methanol | - |
| $(CH_3)_2CH-S-$ | H | H | liquid | - | 105°/0,2mm |
| $C_2H_5S$ | H | H | " | - | 113°/1,6mm |
| ⟨⟩-S- | H | H | 50° | cyclohexane | - |
| H | Cl | $CH_3S-$ | 56° | methanol | - |
| H | H | $HOCH_2CH_2S-$ | 60° | benzene | - |
| $HOCH_2CH_2S-$ | H | H | liquid | - | not dist. |
| H | H | $n-C_6H_{13}S-$ | " | - | 117°/0,15mm |
| H | H | $C_2H_5-CH-S-$<br>$\quad\quad CH_3$ | " | - | 98°/0,2mm |
| H | H | ⟨H⟩-S- | " | - | 115°/0,2mm |

They can be manufactured, for example, by the method described for p-n-butylmercapto-benzaldehyde. Gaseous mercaptans, such as methylmercaptan, are passed in beneath the surface. The ortho-substituted derivatives require a reaction temperature raised by about 10°C to 20°C. Chlorine in the 2- and 4-position in the benzaldehyde is replaced. In 3,4-dichlorobenzaldehyde, the chlorine 3-position remains.

The isolation of high boiling, liquid aldehydes, e.g. o-hydroxyethylsulphonyl-benzaldehyde, is effected advantageously without purification by distillation and only by removal of volatile by-products in vacuo at 100°C. On the other hand, solid aldehydes are filtered off and recrystallised from suitable solvents. It is preferable to use methylene chloride for the extraction of aldehydes which are sparingly soluble in carbon tetrachloride, e.g. p-hydroxyethylsulphonyl-benzaldehyde.

EXAMPLE 5

8.2 g of the compound of the formula (133) in 100 ml of glacial acetic acid are oxidised at reflux temperature over the course of 1 hour by the dropwise addition of 6.9 ml of hydrogen peroxide (0.39 g/ml) in 20 ml of glacial acetic acid. Upon completion of the addition, the reaction mixture is stirred for 1 hour, cooled, and treated with 20 ml of water. The precipitate is filtered off wich suction, washed with glacial acetic acid, and dried. The resulting product (7.5 g) is then acetylated by being boiled for 1/2 hour in 20 ml of pyridine and 10 ml of acetic anhydride. The batch is evaporated to dryness in vaco and the residue is crystallised from chlorobenzene and glacial acid to yield the compound of the formula

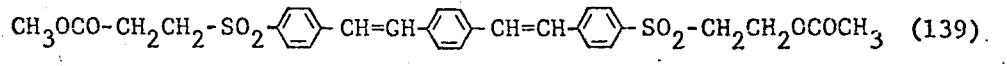

$CH_3OCO-CH_2CH_2-SO_2$-⟨⟩-$CH=CH$-⟨⟩-$CH=CH$-⟨⟩-$SO_2-CH_2CH_2OCOCH_3$ (139)

m.p. 225°C.

EXAMPLE 6

After expulsion of the air by nitrogen, 2.8 g of sodium methylate are added with vigorous stirring to a solution of 8.15 g of p-(n-butylmercapto)-benzaldehyde and 7.57 g of 1,4-bis-(diethoxyphosphonomethyl)-benzene in 50 ml of anhydrous chlorobenzene, in the process of which the temperature is allowed to rise t 50°C. The reaction mixture is stirred for 2 hours at 50°C, then 20 ml of glacial acetic acid and 0.05 g of ammonium molybdate (freshly precipitated from water/glacial acetic acid) are added to the thick, yellow suspension of the disulphide, and a solution of 7.4 ml of hydrogen peroxide (35.1%) in 20 ml of glacial acetic acid is added dropwise at 100°C over the course of 1 hour. The disulphide passes therewith into solution. After it has been stirred for ½ hour at 100°C, the batch is cooled, the crystallised product filtered off and dried, to yield 7.2 g (69% of theory) of the disulphone of the formula (114) with a melting point of 275°C.

The distyrylbenzene derivatives of the general formula

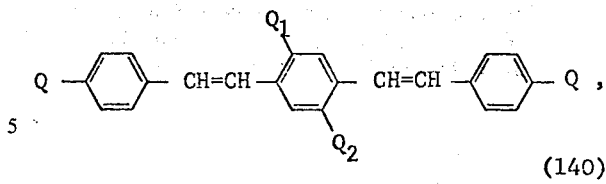

(140)

wherein Q and $Q_1$ have the meanings given in Table V, can be manufactured by the procedures described in Examples 1, 2 and/or 4.

Table V

| Formel Nr. | Q | $Q_1$ | $Q_2$ |
|---|---|---|---|
| (141) | $-SO_2-\langle\rangle-CH_3$ | H | H |
| (142) | $-SO_2-CH_2-\langle\rangle-Cl$ | H | H |
| (143) | $-SO_2-\langle\rangle-CH_2CH_2CH_3$ | H | H |
| (144) | $-SO_2-\langle\rangle-CH(CH_3)-C_2H_5$ | H | H |
| (145) | $-SO_2-\langle\rangle-C(CH_3)_3$ | H | H |
| (146) | $-SO_2-CH_2CH_2CH_2CH_2CH_3$ | H | H |
| (147) | $-SO_2-CH_2CH_2CH(CH_3)_2$ | H | H |
| (148) | $-SO_2-CH(CH_2CH_3)CH_2CH_2CH_3$ | H | H |
| (149) | $-SO_2-\langle\rangle-CH(CH_3)-CH_2CH_2CH_3$ | H | H |
| (150) | $-SO_2-\langle\rangle(CH(CH_3)_2)-CH(CH_3)_2$ | H | H |
| (151) | $-SO_2-\langle\rangle(CH(CH_3)_2)(CH(CH_3)_2)$ | H | H |
| (152) | $-SO_2-\langle\rangle-Br$ | H | H |
| (153) | $-SO_2-\langle\rangle-CH_3$ | H | H |
| (154) | $-SO_2-n-C_4H_9$ | Cl | Cl |
| (155) | $-SO_2-n-C_4H_9$ | $OCH_3$ | $OCH_3$ |
| (156) | $-SO_2-n-C_4H_9$ | $CH_3$ | $CH_3$ |
| (157) | $-SO_2-C_2H_4$ | Cl | H |
| (158) | $-SO_2-C_4H_9$ | Cl | H |
| (159) | $-SO_2CH(CH_3)_2$ | H | H |
| (160) | $-SO_2-C(CH_3)_3$ | H | H |

EXAMPLE 7

A polyester fabric (based on terephthalic acid/ethylene glycol) is padded at room temperature with an aqueous dispersion which contains per litre 2 g of one of the compounds of the formulae (104), (105), (114), (123) or (139), and 1 g of an adduct of about 8 mols of ethylene oxide with 1 mol of p-tert. octylphenol, and dried at about 100°C. The dry material is subsequently subjected for a brief period to a heat treatment of 220°C. The material treated in this way exhibits a strong white effect with good light fastness.

A strong white effect with good light fastness is also obtained by using instead of the polyester fabric described hereinabove a polyester fabric manufactured by co-condensation with 2 to 5 mol % of isophthalic acid-5-sodium sulphonate (Dacron 64).

EXAMPLE 8

100 parts of terephthalic acid ethylene glycol polyester are intimately mixed with 0.05 part of one of the compounds of the formulae (100), (101) (102) (104), (105), (107), (108), (109), (110), (114), (123), (124), (125) or (139) and the mixture is fused at 285°C with stirring. The spinning melt is spun through conventional jets to give strongly whitened polyester fibres with good fastness to light.

EXAMPLE 9

An intimate mixture of 100 parts of polyvinyl chloride, 3 parts of stabiliser (Advastat BD 100: Ba/Cd complex), 2 parts of titanium dioxide, 59 parts of dioctyl phthalate, and 0.01 to 0.2 parts of one of the compounds of the formula (101), (104), (105), (114), (121), (123), (124) or (139), are rolled out to a sheet on a calender at 150°C. to 155°C.

The so obtained opaque polyvinyl chloride sheet possesses a high white content of good fastness to light.

EXAMPLE 10

A coating composition which consists of 10 g of polyacrylonitrile, 0b 0.2 g of titanium dioxide (anatase modification) as delustrant, and 40 ml of dimethyl formamide, and which contains 5 mg of one of the compounds of the formula (100), (101), (102), (106) or (107), is poured on a glass plate and drawn out with a metal rod to a thin film. After it has dried, the film is strongly whitened.

EXAMPLE 11

A 15% coating composition which consists of acetyl cellulose in acetone and which — based on the plastics dry weight — contains 2% of anatase (titanium dioxide) as delustrant, and 0.04% of one of the compounds of the formulae (104), (114) or (139), is poured on a glass plate and drawn out to a thin sheet with a metal rod. After it has dried, the sheet exhibits a substantially higher degree of whiteness than a similarly prepared sheet which contains no optical brightener.

EXAMPLE 12

1000 parts of granulated polyamide 6 are mixed for 12 hours in a roller with 3 parts of titanium dioxide (rutile modification) and 1 part of one of the compounds of the formulae (100) or (101). The mixture is fused in the absence of atmospheric oxygen and the melt is spun in the usual manner. The resulting threads are strongly whitened.

EXAMPLE 13

A 27% coating which consists of polyurethane in ethyl acetate and which — based on the plastics dry weight — contains 2% of titanium dioxide (anatase modification), 5% each of a stabiliser and a catalyst as well as 0.5% of a compound of the formulae (104), (105), (119) or (139), is poured on a glass plate and drawn out to a thin film with a metal rod. After it has dried, the film is strongly whitened.

EXAMPLE 14

A polyamide fibre fabric (Perlon) is put at 60°C, in the liquor ratio of 1:40, into a batch containing (based on the weight of the fabric) 0.1% of one of the brighteners of the formulae (26) or (27) as well as, per litre, 1 g of 80% acetic acid and 0.25 g of an adduct of 30 to 35 mols of ethylene oxide with 1 mol of commercial stearyl alcohol. The batch is heated within 30 minutes to boiling temperature and kept for 30 minutes at the boil. After the fabric has been rinsed and dried, there is obtained a strong white effect of good fastness to light.

Similarly good white effects are obtained by using a fabric made from polyamide 66 (nylon) instead of polyamide 6.

Finally, it is also possible to carry out the process under HT conditions, e.g. over the course of 30 minutes at 130°C. For this kind of application, it is advisable to add 3 g/l of hydrosulphite to the solution.

Similar results are obtained with the compounds of the formulae (119) or (139).

EXAMPLE 15

A cellulose acetate fabric is put into an aqueous bath at 50°C in the liquor ratio 1:30 to 1:40. The bath contains 0.15% (based on the weight of the fabric) of the compound of the formula (139). The temperature of the treatment bath is brought to 90°C – 95°C and kept at this temperature for 30 to 40 minutes. After the fabric has been rinsed and dried, a good white effect is obtained.

I claim:

1. A distyrylbenzene derivative of the formula $$R_1O_2S \overset{}{\underset{X_1}{\diagup\!\!\!\diagdown}} \overset{Y_1}{\underset{}{\diagup\!\!\!\diagdown}} -CH=CH- \overset{}{\underset{Y_1}{\diagup\!\!\!\diagdown}} -CH=CH- \overset{SO_2R_1}{\underset{X_1}{\diagup\!\!\!\diagdown}}$$

wherein $R_1$ represents alkyl with 1 to 6 carbon atoms or alkyl with 1 to 6 carbon atoms substituted by chlorine or hydroxy, cyclohexyl, benzyl or benzyl substituted in the phenyl moiety by chlorine or methyl or phenyl or phenyl substituted by chlorine, bromine, or alkyl with 1 to 6 carbon atoms, $X_1$ represents hydrogen, chlorine, methyl, or alkylsulphony with 1 to 4 carbon atoms, and $Y_1$ represents hydrogen, chlorine, methyl, or methoxy.

2. A distyrylbenzene derivative according to claim of the formula $$\overset{}{\underset{R_2O_2S}{\diagup\!\!\!\diagdown}} -CH=CH- \overset{Y_2}{\underset{Y_2'}{\diagup\!\!\!\diagdown}} -CH=CH- \overset{SO_2R_2}{\underset{}{\diagup\!\!\!\diagdown}}$$

wherein $R_2$ represents alkyl with 1 to 6 carbon atoms or alkyl with 1 to 6 carbon atoms substituted by cyclohexyl or benzyl, substituted in the phenyl moiety by chlorine or methyl, or phenyl or phenyl substituted by chlorine or alkyl with 1 to 6 carbon atoms, and $Y_2$ and $Y'_2$ each independently represents hydrogen or chlorine.

3. A distyrylbenzene derivative according to claim 1, of the formula

wherein $R_3$ represents alkyl with 1 to 6 carbon atoms, or phenyl or phenyl substituted by chlorine or alkyl with 1 to 6 carbon atoms.

4. A distyrylbenzene derivative according to claim 1, of the formula

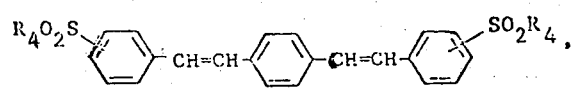

wherein $R_4$ represents alkyl with 1 to 6 carbon atoms an alkyl with 1 to 16 carbon atoms substituted by chlorine, hydroxy, or represents cyclohexyl.

5. A dystyrylbenzene derivative according to claim 1, of the formula

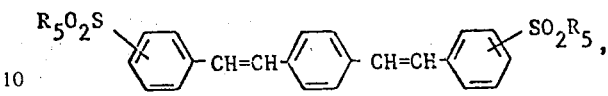

wherein $R_5$ represents alkyl with 1 to 6 carbon atoms.

6. A distyrylbenzene derivative according to claim 1, of the formula

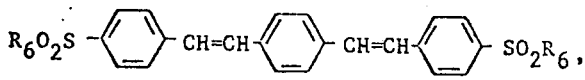

wherein $R_6$ represents alkyl with 1 to 6 cargon atoms or phenyl.

* * * * *

UNITED STATES PATENT AND TRADEMARK OFFICE
CERTIFICATE OF CORRECTION

PATENT NO. : 3,956,395
DATED : May 11, 1976
INVENTOR(S) : HANS RUDOLF MEYER

It is certified that error appears in the above-identified patent and that said Letters Patent are hereby corrected as shown below:

Column 1, after HANS RUDOLF MEYER, Binningen, Switzerland should read   -- ASSIGNOR TO CIBA-GEIGY CORPORATION --

Column 22, line 61, claim   should read -- claim 1 --.

Signed and Sealed this

Thirteenth Day of July 1976

[SEAL]

Attest:

RUTH C. MASON
*Attesting Officer*

C. MARSHALL DANN
*Commissioner of Patents and Trademarks*